US00PP19710P3

(12) United States Plant Patent
LaBonte et al.

(10) Patent No.: US PP19,710 P3
(45) Date of Patent: Feb. 10, 2009

(54) SWEETPOTATO PLANT NAMED 'EVANGELINE'

(50) Latin Name: *Solanum tuberosum*
Varietal Denomination: Evangeline

(75) Inventors: Don R. LaBonte, Baton Rouge, LA (US); Arthur Q. Villordon, Baton Rouge, LA (US); Christopher A. Clark, Baton Rouge, LA (US)

(73) Assignee: Board of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 91 days.

(21) Appl. No.: 11/789,681

(22) Filed: Apr. 25, 2007

(65) Prior Publication Data

US 2008/0271216 P1 Oct. 30, 2008

(51) Int. Cl.
*A01H 5/00* (2006.01)

(52) U.S. Cl. ..... Plt./258
(58) Field of Classification Search ..... Plt./258
See application file for complete search history.

*Primary Examiner*—Kent L Bell
(74) *Attorney, Agent, or Firm*—John H. Runnels; Bonnie J. Davis; James C. Carver

(57) ABSTRACT

A new variety of sweetpotato identified as 'Evangeline' is disclosed having disease resistance to both southern root-knot nematode and soil rot, a deep orange flesh, a high sucrose content, and high yield characteristics.

3 Drawing Sheets

This invention pertains to a new and distinct variety of sweetpotato.

BACKGROUND OF THE INVENTION

Sweetpotatoes, unlike Irish potatoes (*Solanum tuberosum*), are not tuber propagated plants. A "tuber" is a short, thickened portion of an underground branch. Along a tuber "eyes" are found, each of which comprises a ridge bearing a scale-like leaf (analogous to a branch leaf) having minute meristematic buds in the axial of the leaf. By contrast, sweetpotato roots are developmentally and anatomically true roots, lacking meristematic buds, and are not derived from an underground branch. Sweetpotatoes do not form tubers.

SUMMARY OF THE INVENTION

Genus and Species Name

This new and distinct sweetpotato variety, *Ipomoea batatas* (L.) Lam., demonstrates superior disease resistance to southern root-knot nematode, and exhibits a deep orange flesh and a higher sucrose content compared to the 'Beauregard' variety. It also demonstrates a resistance to soil rot and high yield characteristics similar to 'Beauregard.'

Variety Denomination

This new and distinct sweetpotato variety is identified as 'Evangeline', and is characterized by its dark orange flesh, elliptical roots, and higher sucrose content.

BRIEF DESCRIPTION OF THE DRAWINGS

The file of this patent contains at least one photograph executed in color. Copies of this patent or patent application with color drawing(s) will be provided by the Patent and Trademark Office upon request and payment of the necessary fee.

DETAILED BOTANICAL DESCRIPTION

This new variety of sweetpotato, named 'Evangeline', resulted from an open pollination in 1998 to the Louisiana Agricultural Experiment Station female parent 'L94-96' ('Bienville' patented U.S. Plant Pat. No. 15,380 P3). The male parent was unknown. One patented sweetpotato ('L96-117' U.S. Plant Pat. No. 15,038 P2) was among the potential pollen sources in the nursery. Both patents were held by the Louisiana Agricultural Experiment Station in Baton Rouge, La. 'Evangeline' was developed by the Louisiana Agricultural Experiment Station in Baton Rouge, La., to provide a variety with characteristics similar to 'Beauregard' (unpatented), but with improved resistance to southern root-knot nematode and higher sucrose content. 'Evangeline' was characterized by a darker orange flesh. The female parent 'Bienville' had similar disease resistant characteristics to that of 'Evangeline'.

Plants of 'Evangeline' and 'Bienville' can be distinguished by lighter green vines [2.5 G (green) Y (yellow) 5/6] for 'Evangeline' versus green vines [7.5 G (green) Y (yellow) (5/6)] for 'Bienville'. Color terminology used herein is in accordance with the Munsell® Book of Color (Munsell Color, GretagMacbeth LLC, 617 Little Britain Road, New Windsor, N.Y. 125536148). The color descriptions and color illustrations are as nearly true as is reasonably possible. However, it is understood that both color and other phenotypic expressions described herein may vary from plant to plant with differences in growth, environment and cultural conditions, without any change in the genotype of the variety 'Evangeline'.

'Evangeline' roots were stored during the winter in Chase, La. 'Evangeline' was planted the following spring, resulting in approximately 8–10 sprouts per root. Cuttings from the sprouts were transplanted successfully for asexual reproduction. Asexual propagation of the new cultivar by cuttings has shown that the unique features of this new sweetpotato were stable and that the plant reproduced true to type in successive generations of asexual propagation. Plants described herein were approximately 90–110 days in age from planting in full sun field plantings.

Figure 1:
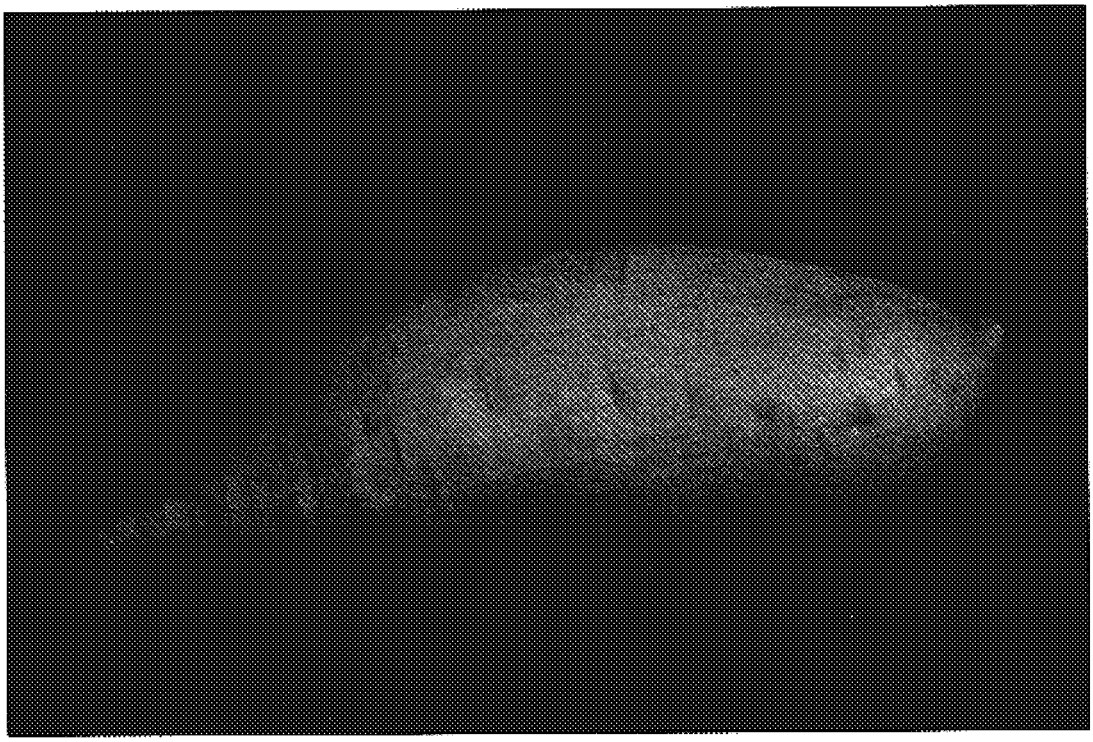
FIG. 1 is a color photograph of the fleshy root form of the novel variety of sweetpotato identified as 'Evangeline'.
Figure 2:
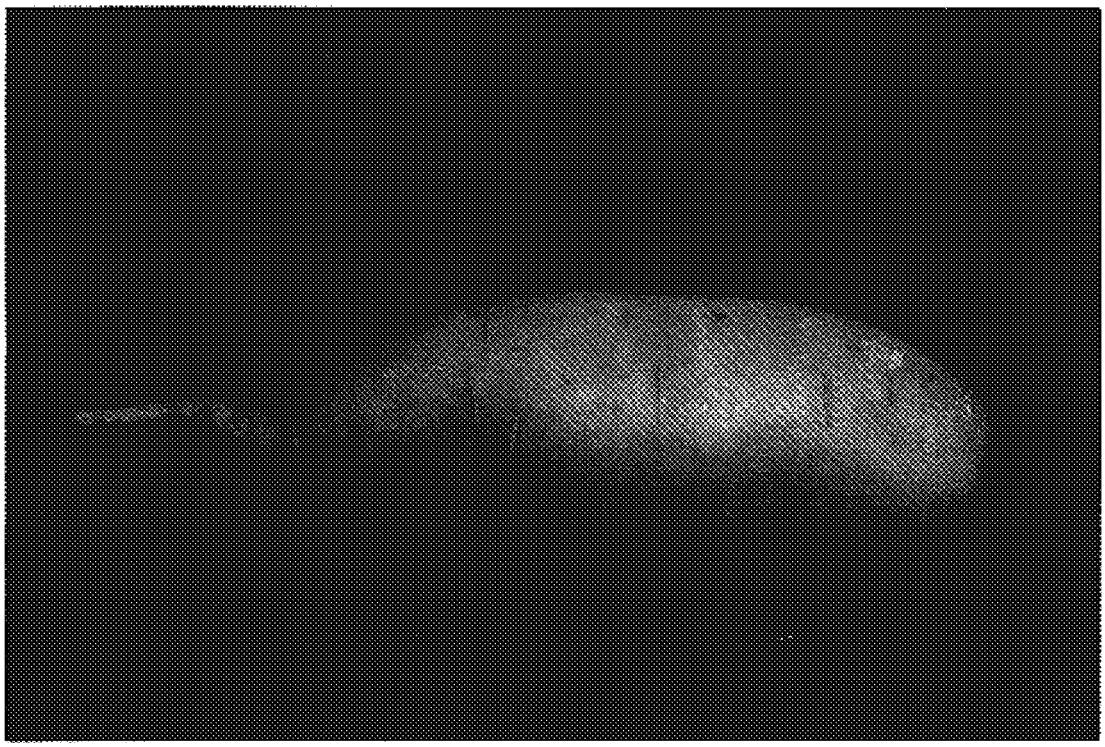
FIG. 2 is a color photograph of the fleshy root form of the sweetpotato variety identified as 'Beauregard'.

FIG. 1 depicts the fleshy root form of the 'Evangeline' sweetpotato. The skins vary in color from light to medium rose, which is similar to 'Beauregard', both at harvest and after several months of storage as shown in Table 1. Munsell® Book of Color values for skin and flesh for both 'Evangeline' and 'Beauregard' storage roots at harvest are shown in Table 1. The 'Beauregard' sweetpotato is depicted in FIG. 2. The skin for both 'Evangeline' and 'Beauregard' was smooth. 'Evangeline' storage roots were elliptical without lobing, and they were not as long as 'Beauregard'. The 'Evangeline' cortex was 4–5 mm in depth.

TABLE 1

| Variable | Variety | Color |
|---|---|---|
| Skin | 'Evangeline' | 7.5 R (red) 5/6 |
| | 'Beauregard' | 7.5 R (red) 5/6 |
| Flesh | 'Evangeline' | 2.5 Y (yellow) R (red) 7/12 |
| | 'Beauregard' | 2.5 Y (yellow) R (red) 7/10 |

Figure 3:
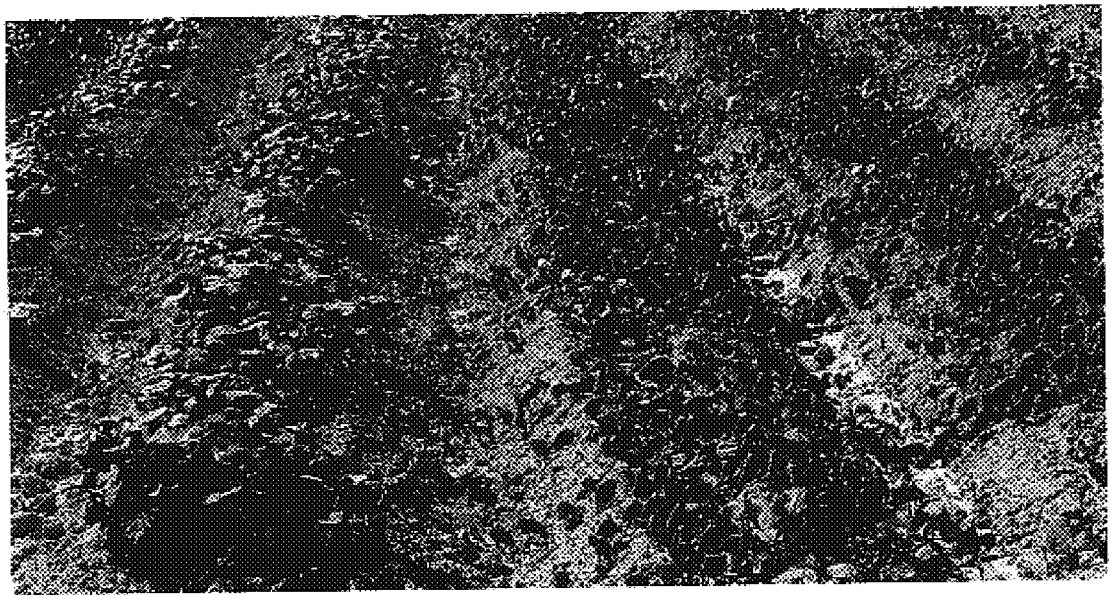
FIG. 3 is a color photograph of the canopy biomasses of the novel variety of sweetpotato identified as 'Evangeline' (shown on the left side of the photograph) and the variety identified as 'Beauregard' (shown on the right side of the photograph).

FIG. 3 depicts the canopy biomass of both 'Evangeline' sweetpotatoes and 'Beauregard' sweetpotatoes. 'Evangeline' has green-stemmed vines [2.5 G (green) Y (yellow) (5/6)] from the apex to the crown of the roots. The 'Evangeline' canopy biomass appears to be greater than that for 'Beauregard'. The 'Evangeline' canopy architecture was upright (30 cm in height from the soil surface) and erect prior to spreading (80 cm radius), while 'Beauregard' exhibited a prostrate growth habit (23 cm in height from the soil surface). For 'Evangeline', four to five main vines arose from the main stem near the soil surface. The stem giving rise to these vines was 2.5 cm in diameter; the 4–5 lateral vines were 120 cm in length with diameters of about 0.6 cm at 65 cm from the base, diameters of about 0.7 cm at the base of the vine, and diameters of about 0.46 cm at the first internode of the first fully developed leaf from the apex. Three to four lateral branches arose from each of the main vines. At the first internode from the apex, the internode length was about 4.4 cm between the first and second fully developed leaves. Internode lengths for other sections of the vine averaged about 4.6 cm. Unfolded immature leaves were dark purple [5R (red) P (purple) (3/2)] for the upper and lower surface, which changed gradually over one to two nodes from the apex to dark green upper surface [7.5 G (green) Y (yellow) (4/4)] to green lower surface [5 G (green) Y (yellow) (4/4)]. Mature leaves at five nodes from the apex had an acute apex and mostly a cordate base and a smooth leaf margin. Mature leaves were about 10.4 cm long and 10.9 cm wide. Abaxial and adaxial veins were green [5 G (green) Y (yellow) (4/4)]. The petiole was red [5R (red) (4/6)] at its junction with the leaf, which quickly changed to green [5 G (green) Y (yellow) (5/6)] and then remained green at the nodal junction. The petiole was 9–10 cm long at five nodes from the apex, and 3–4 mm in diameter at 5 cm from the leaf junction. The dormant nodal meristem also was green [2.5 G (green) Y (yellow) (5/6)]. Immature leaves of 'Beauregard' were sometimes dark purple, similar to 'Evangeline', but the 'Beauregard' leaves had zones of green [2.5 G (green) Y (yellow)] on portions of the leaf upper surfaces. The coloration was also more variable on 'Beauregard' when compared to 'Evangeline'.

A typical inflorescence of 'Evangeline' displayed three flowers per peduncle. Peduncles were green [2.5 G (green) Y (yellow) (5/6)], about 5 cm long, and about 2.3 mm in diameter. Individual flowers were about 3 cm long from the base of the calyx. The fused flower petals formed a pentagonal pattern with smooth edges. The inner throat of the corolla appeared purple [2.5 R (red) P (purple) (3/6)]. The inner and outer limbs of the corolla (corollas outermost area, distal from the calyx) were very light purple [5 P (purple) (6/6)]. The five sepals comprising the calyx were elliptic with a cordate apex and appeared to be green [2.5 G (green) Y (yellow) (8/4)]; three of these sepals were about 9 mm long and 3.6 mm wide. Two other sepals (interspersed) were about 2.2 mm wide. Sepal margins were smooth. Stigmata were about 1.7 cm long and appeared to be purple [5 R (red) P (purple) (6/6)]. Five stamens, which are inferior to stigmata, were attached to the ovary. No fragrance was present.

Example 1

Tests Conducted

To confirm that 'Evangeline' was a new variety, controlled tests (e.g., pathogen responses and yield) were conducted in Baton Rouge, La. 'Beauregard' was selected for comparison because of its dominance in commercial United States sweetpotato acreage. Diseases that commonly affect the growth of sweetpotatoes were selected to test for pathogen responses in both varieties. Scions of 'Evangeline' and 'Beauregard' reacted similarly to most diseases evaluated in the controlled tests. 'Evangeline' and 'Beauregard' were intermediate to resistance for soil rot caused by *Streptomyces ipomoeae* (Person & W. J. Martin) Waksman & Henrici. 'Evangeline' and 'Beauregard' showed similar resistance to Fusarium wilt or stem rot caused by *Fusarium oxysporum* Schlect. f. sp. *batatas* (Wollenw.) Snyd. & Hans.

Nematode reproduction was measured in greenhouse tests. 'Evangeline' was highly resistant to southern root-knot nematode, *Meloidogyne incognita* (Kofoid & White 1919) Chitwood 1949. 'Beauregard' was less resistant to southern root-knot nematode. 'Evangeline' and 'Beauregard' exhibited similar resistance to *Fusarium* root rot caused by *Fusarium solani* (Sacc.) Mart. emend. Snyd. & Hans. 'Evangeline' and 'Beauregard' storage roots both were susceptible to bacterial soft rot caused by *Erwinia chrysanthemi* Burkholder, McFadden & Dimock. 'Evangeline' and 'Beauregard' both were resistant to *Rhizopus* soft rot caused by *Rhizopus stolonifer* (Ehr. ex. Fr.) Lind. Incidences of circular spot caused by *Sclerotium rolfsii* Sacc. were similar for 'Evangeline' and 'Beauregard'.

'Evangeline' did not appear to show any novel insect resistance. Both 'Evangeline' and 'Beauregard' showed similar levels of susceptibility to insect pests, for example, banded Cucumber Beetles (*Diabrotica balteata* LeConte), white grubs (*Plectris aliena* Chapin or *Phyllophaga* spp.), and sweetpotato weevils (*Cylas formicarius* (*fab.*)).

To determine yield production, complete-block trials using four replications of 'Evangeline' and 'Beauregard' each were conducted in Chase, La. in 2005. 'Evangeline' and 'Beauregard' sweetpotato plants were transplanted in randomized complete-block trials at 31 cm spacings in Gilbert silt loam soil in Chase, La. Each block/plot was fertilized with 250 pounds per acre of a mixed fertilizer comprising 13% N, 13% $P_2O_5$, and 13% $K_2O$. 'Evangeline' was compared to 'Beauregard' at early, middle, and late transplanting dates at each location beginning in May-June. Average yields were measured for the following grades of roots: U.S. #1 (51–89 mm in diameter, 76–229 mm long); Canner (25–51 mm in diameter, 51–178 mm long); and Jumbo (larger than U.S. #1 in diameter, length or both, and without objectionable defects). A typical marketable root of 'Evangeline' was 140–150 mm long, 60–70 mm in diameter, with mostly round-elliptic in shapes. The base or distal end tended to be more elongated in comparison to slightly rounder apex (proximal end). U.S. #1 roots typically weighed 150–190 g.

The early transplanting date trial was conducted in Chase, La. 'Evangeline' and 'Beauregard' were transplanted on Jun. 9, 2005, and harvested on Sep. 23, 2005 (106 days after planting). Average yields, measured as Metric Tons per Hectare ($MT \cdot ha^{-1}$), are shown in Table 2.

TABLE 2

| Selection | US#1† | Canners† | Jumbos† | TMY‡† |
|---|---|---|---|---|
| 'Evangeline' | 21.7a | 5.6a | 2.8b | 30.1a |
| 'Beauregard' | 19.2a | 2.5b | 15.0a | 36.8a |
| Least Significant Difference LSD (P < 0.05) | 10.5 | 2.5 | 8.3 | 12.6 |

†Average yields in $MT \bullet ha^{-1}$ of varieties followed by a common letter do not differ significantly
(P < 0.05) according to Duncan's Multiple Range Test.
TMY‡= total marketable yield A second transplanting date trial was also conducted at in Chase, La. on Jun. 16, 2005, and harvested on Sep. 23, 2005 (99 days after planting). Average yields ($MT \cdot ha^{-1}$) of 'Evangeline' and 'Beauregard' are shown in Table 3.

TABLE 3

| Selection | US#1† | Canners† | Jumbos† | TMY‡† |
|---|---|---|---|---|
| 'Evangeline' | 21.0a | 6.8a | 2.7b | 29.9a |
| 'Beauregard' | 22.3a | 8.2a | 6.6a | 32.3a |
| Least Significant Difference LSD (P < 0.05) | 6.5 | 3.1 | 3.1 | 5.6 |

†Average yields in $MT \bullet ha^{-1}$ of varieties followed by a common letter do not differ significantly
(P < 0.05) according to Duncan's Multiple Range Test.
TMY‡= total marketable yield A late transplanting date trial was also conducted in Chase, La. on Jul. 11, 2005, and harvested on Oct. 18, 2005 (99 days after planting). Average yields ($MT \cdot ha^{-1}$) by grade are shown in Table 4.

TABLE 4

| Selection | US#1† | Canners† | Jumbos† | TMY‡† |
|---|---|---|---|---|
| 'Evangeline' | 8.4a | 8.8a | 0.3b | 17.5b |
| 'Beauregard' | 12.1a | 6.9a | 3.6a | 22.5a |
| Least Significant Difference LSD (P < 0.05) | 4.1 | 2.3 | 1.6 | 4.2 |

†Average yields in $MT \bullet ha^{-1}$ of varieties followed by a common letter do not differ significantly
(P < 0.05) according to Duncan's Multiple Range Test.
TMY‡= total marketable yield As shown in Tables 2–4, 'Evangeline' produced yields comparable to 'Beauregard' at two early transplanting dates (112% and 94% of 'Beauregard' for U.S. #1 grade; 82% and 93% of 'Beauregard' for total marketable yield). At a later planting date, 'Evangeline' had yields that were slightly less than those of 'Beauregard'. Replicated plots at other farms have not shown any predisposition of 'Evangeline' to have low yield for early, middle, or late season plantings. 'Evangeline' had harvestable roots approximately 110–115 days after planting, which is typical development time for sweetpotatoes. There was a tendency for 'Evangeline' to produce fewer Jumbos in comparison to 'Beauregard', but since this root category is of less economic value, this feature may not be significant.

Sugar profiles for baked 'Evangeline' and 'Beauregard' are shown in Table 5. For this test, roots were stored for five months after which they were baked at 190° C., for approximately 2.0 h. In a second test, roots were stored for three months and then baked at 190° C. for approximately 2.0 h. Sucrose content in baked 'Evangeline' was nearly twice that found in baked 'Beauregard'. In contrast, 'Beauregard' had nearly twice as much maltose as 'Evangeline'. Total sugar content did not differ much between 'Evangeline' and 'Beauregard'. However, maltose is rated to be about 50 percent less sweet than sucrose. Therefore, 'Evangeline' sweetpotatoes exhibited a greater sugar profile than 'Beauregard' sweetpotatoes.

TABLE 5

| Selection | Fructose‡ | Glucose‡ | Sucrose‡ | Maltose‡ | Total sugars†‡ |
|---|---|---|---|---|---|
| 'Evangeline' | 5.3 (2005) | 4.6 (2005) | 62.5 (2005) | 26.5 (2005) | 98.9 (2005) |
| | 5.0 (2006) | 5.8 (2006) | 64.1 (2006) | 34.8 (2006) | 109.7 (2006) |
| 'Beauregard' | 6.7 (2005) | 8.9 (2005) | 36.0 (2005) | 51.2 (2005) | 102.8 (2005) |
| | 6.1 (2006) | 8.9 (2006) | 22.3 (2006) | 54.3 (2006) | 91.6 (2006) |

†Total sugars = fructose + glucose + maltose + sucrose.
‡$mg \bullet g^{-1}$ fresh weight basis.

'Evangeline' should be a valuable commercial sweetpotato variety. 'Evangeline' produced plants (sprouts) comparable to 'Beauregard', although the number of plants per acre was slightly greater for 'Beauregard'. Days to harvest for 'Evangeline' were similar to 'Beauregard'. 'Evangeline' exhibited superior flesh color and higher desirable sugar content. 'Evangeline' is ideally suited for production on land infested with southern root-knot nematode and soil rot.

We claim:

1. A new and distinct variety of *Ipomoea batatas* plant named 'Evangeline' as described and illustrated in the specification herein.

* * * * *